United States Patent [19]

Harris et al.

[11] Patent Number: 5,096,670
[45] Date of Patent: Mar. 17, 1992

[54] AUTOMATED PATIENT SAMPLE ANALYSIS INSTRUMENT

[76] Inventors: Paul C. Harris, 8717 191st Pl. Southwest, Edmonds, Wash. 98020; Curtis C. Genstler, 8602 137th Northeast, Redmond, Wash. 98052

[21] Appl. No.: 349,901

[22] Filed: May 8, 1989

Related U.S. Application Data

[63] Continuation of Ser. No. 925,316, Oct. 31, 1986, abandoned.

[51] Int. Cl.⁵ ............................................. G01N 35/00
[52] U.S. Cl. ..................................... 422/65; 356/244; 356/246; 422/63; 422/66; 422/67; 422/73; 422/100; 422/102; 422/104
[58] Field of Search ........................ 422/63-67, 422/73, 100, 102, 104; 356/244, 246

[56] References Cited

U.S. PATENT DOCUMENTS

| | | | |
|---|---|---|---|
| 3,526,480 | 9/1970 | Findl et al. | 422/66 |
| 3,556,731 | 1/1971 | Martin | 422/65 |
| 3,902,971 | 9/1975 | Fletcher et al. | |
| 4,154,795 | 5/1979 | Thorne | 422/102 |
| 4,403,687 | 9/1983 | Stevens et al. | |
| 4,431,924 | 2/1984 | Suovaniemi et al. | 356/244 |
| 4,510,119 | 4/1985 | Hevey | 422/71 |
| 4,528,159 | 7/1985 | Liston | |
| 4,545,958 | 10/1985 | Dopatka | 436/809 |
| 4,595,562 | 6/1986 | Liston et al. | 422/102 |
| 4,643,879 | 2/1987 | Hanaway | 422/102 |
| 4,678,894 | 7/1987 | Shafer | 436/809 |
| 4,681,742 | 7/1987 | Johnson | 422/100 |
| 4,701,754 | 10/1987 | Provonchee | 422/67 |

FOREIGN PATENT DOCUMENTS

57-111451  7/1982  Japan ................................. 422/73

*Primary Examiner*—Robert J. Warden
*Assistant Examiner*—Timothy M. McMahon

[57] ABSTRACT

An automated sample analysis instrument positively identifies and maintains the identity of a plurality of patient samples contained in individual sample containers. The invention prevents sample misidentification, especially when patient sample must be transferred from one sample container to reaction wells in Microtiter® plates. Rows of reaction wells in Microtiter® plates are processed in parallel so the difference in reaction time between any two wells on a plate is four minutes or less. Reaction wells are washed with high-pressure jets of wash solution and are aspirated so as to advantageously utilize fluid meniscus on top of fluid contained in the wells. The apparatus can be adjusted to perform a variety of different ELISA-type tests.

23 Claims, 7 Drawing Sheets

FIG. 5
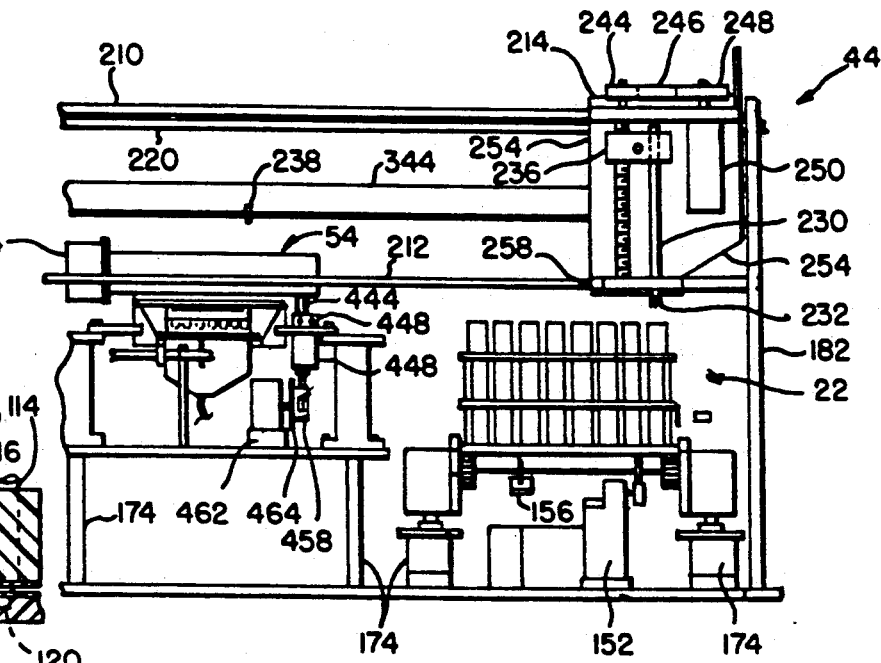
FIG. 6
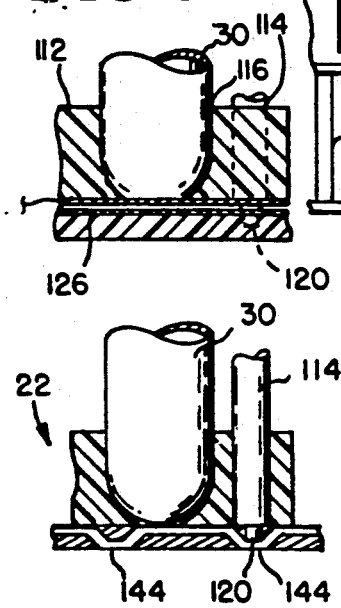
FIG. 7
FIG. 8
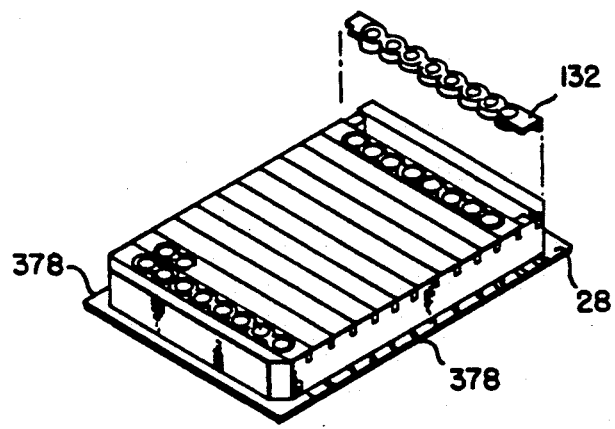
FIG. 9
FIG. 10
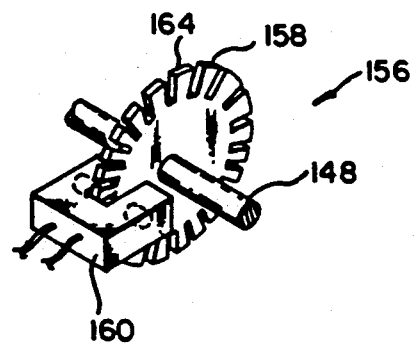
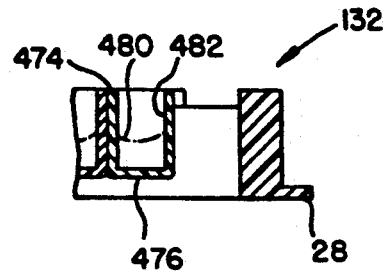

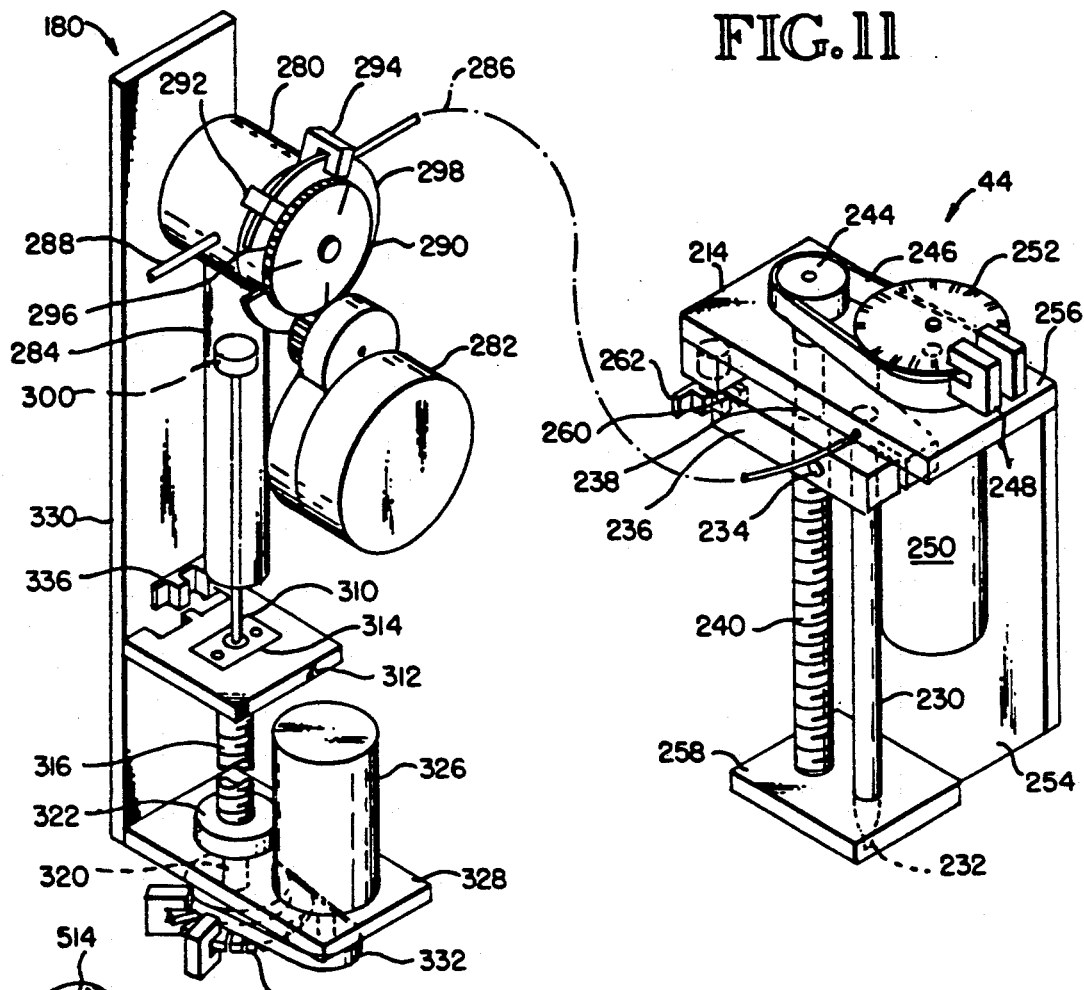
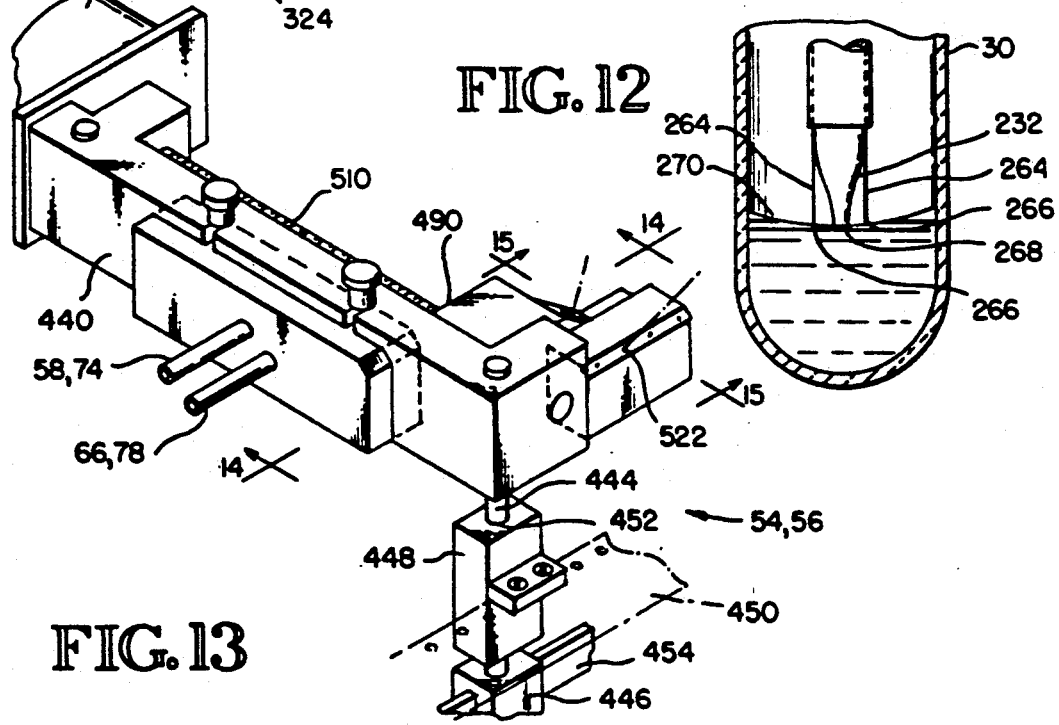

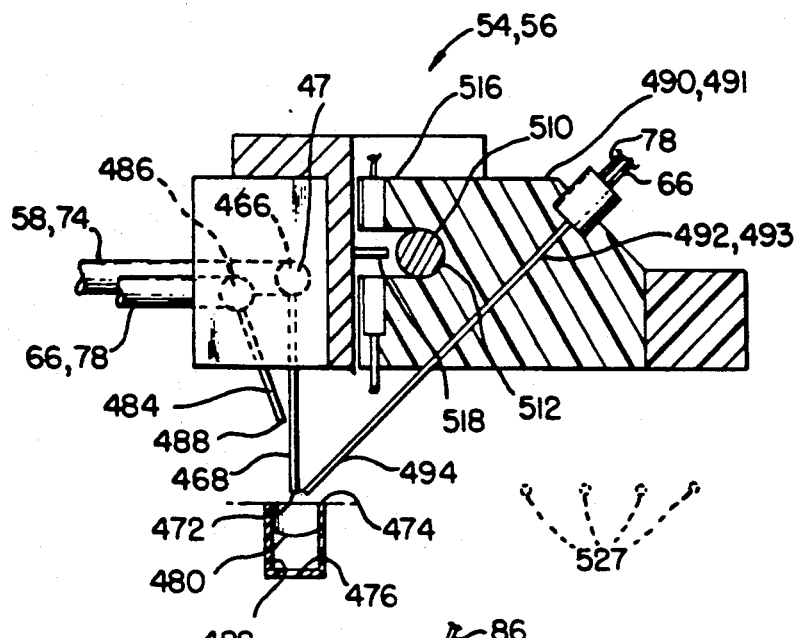
FIG. 14
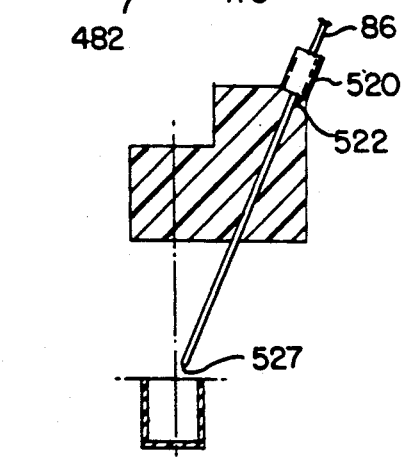
FIG. 15
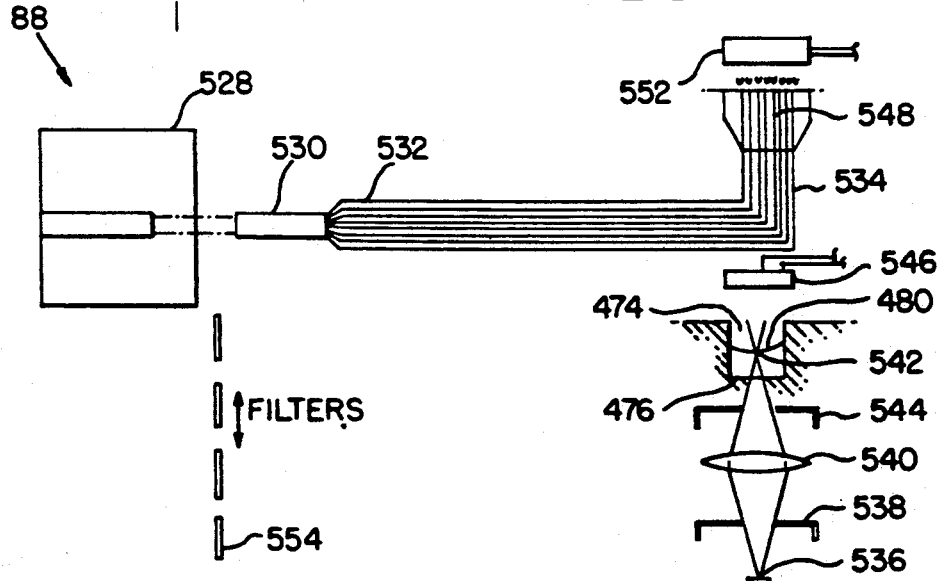
FIG. 16
FIG. 17

AUTOMATED PATIENT SAMPLE ANALYSIS INSTRUMENT

This is a continuation Ser. No. 06/925,316 filed Oct. 31, 1986 now abandoned.

DESCRIPTION

1. Technical Field

The invention relates to methods and apparatus for conducting enzyme-linked immunoabsorbent assay (ELISA) tests. More specifically, the invention relates to an automatic apparatus for performing ELISA tests.

2. Background Art

Recent advances in biotechnology have permitted the development of ELISA tests for various infectious agents. Such testing has become increasingly important, especially for blood screening purposes, to maintain the integrity of hospital blood banks. The introduction of human error, the limited speed of manual processing techniques, and equipment limitations have prevented ELISA tests from achieving their full potential of reliability. Furthermore, preparation and performance of the assay may be tedious when a large number of patient samples are to be tested.

Typically, ELISA tests rely on the use of Microtiter ® plates which have reaction wells coated with a first reactant. Patient sample, in the form of serum or plasma suspected of containing an analyte (i.e., an antibody or antigen) which is capable of specifically binding with the first reactant, is added to the wells. After an incubation period, patient sample and any unbound analyte are removed and the reaction wells carefully washed. A reporter/second reactant conjugate is then added to the reaction wells and incubated. At the end of this second incubation period, unbound conjugate is removed, the wells washed again, and a chromogenic substrate added and allowed to incubate for a third incubation period. A color will then develop in proportion to the amount of analyte which has bound to the first reactant. At the end of the third incubation period, the reactions in each reaction well are stopped by the addition of an acid solution. The optical density of the resulting fluid indicates the quantity of bound analyte, which is indicative of the quantity of the infectious agent or the antibody thereto in the samples. Positive and negative controls are included in the assay to determine a cutoff absorbance, which indicates whether the sample is positive or negative.

The chemical reactions are time-, temperature- and concentration-dependent. Manual methods of conducting ELISA tests invariably result in different processing times for different samples. For example, in a Microtiter ® plate containing 96 reaction wells, 96 patient samples must be prepared. In one test prepared for the detection of acquired immune deficiency syndrome (AIDS) antibodies, patient samples must first be diluted in two steps with a diluent (1:400) before the resulting dilution may be added to the reaction wells. The technician must also accurately identify which patient sample is being placed in which reaction well and usually records this information on a grid which identifies the coordinates of the reaction wells. Preparation of the patient samples, transfer of the samples (or diluted samples), and sample identification can take up to an hour or more for a single assay. Therefore, the reaction between the first reactant and analyte in the first loaded reaction well may have started substantially before the reaction in the last loaded reaction well, resulting in what is known as "front-to-back error."

Similar variations in reactions times may occur, especially if the reaction wells are washed manually and/or loaded with reporter/second reactant conjugate, chromogenic substrate, and stop solution manually. Where automated plate washers are used, it has been found that presently available washers do not completely empty the reaction wells of fluid, requiring the reaction wells to be blotted by the technician.

A further problem in the manual preparation of Microtiter ® plates is cross-contamination between patient samples. Typically, technicians use pipettes for drawing patient sample from test tubes (and for dilution of those samples) which have disposable tips. If patient sample is inadvertently drawn too far into the pipette, disposal of the pipette tip does not prevent contamination of the next sample. It is often difficult for a technician to detect this error or to later identify an anomalous test result as having been caused by this procedural error.

Temperature variations during the incubation periods among the wells in one plate also provide substantial variations in reaction rates in the reaction wells and, therefore, in the optical density of the fluid contained therein. Typically, the Microtiter ® plates are incubated in what are essentially small ovens. These incubators rely primarily on convection to distribute heat evenly among the reaction wells. It is well known that a significant "edge effect" occurs in incubators. This edge effect is the result of a temperature gradient between the center and edges of the plate which is due to the inability of convection currents to evenly heat the plate.

The most serious problem in achieving test reliability and repeatability has been found to be sample misidentification. This error primarily occurs due to transcription errors and sample transfer errors. In the first case, it is known that technicians sometimes incorrectly record the location of a patient sample in a test tube rack. In the second case, technicians have been known to transfer patient samples from a sample test tube to the wrong reaction well in the Microtiter ® plate. Although transcription procedures and handling techniques have been developed to avoid such errors, they are still known to occur. It is possible that the tedious nature of preparing and transferring samples may lead technicians to devote less than their full attention to the task at hand. Once a transcription or sample transfer error has occurred, it is often impossible for the technician to retrace his or her steps to rectify the mistake. Often, the fact that an error has occurred may not be recognized until the assay has been completed and positive results have been impossible to duplicate in a subsequent verification test. In this case, the entire assay must be performed again.

In view of the above, a need exists for a method and an apparatus which substantially reduce the possibility of human error, increase the accuracy, speed and reliability in tests of this type, and which overcome the performance limitations of equipment presently available.

DISCLOSURE OF THE INVENTION

The invention comprises an automated apparatus employing methods which positively identify and maintain the identity of a plurality of patient samples contained in individual sample containers. The apparatus automatically prepares dilutions of patient samples and transfers patient samples and/or patient sample dilutions to one or more Microtiter ® plates. The Microtiter ® plates are processed by a processing line which employs parallel/serial processing. That is, all of the reaction wells in a row on both the Microtiter ® plates are processed simultaneously.

In a preferred embodiment, one row of eight reaction wells is processed every four minutes. Therefore, in a Microtiter ® plate containing twelve rows, with eight reaction wells in each row, the maximum processing time difference between any two reaction wells is only four minutes. Correspondingly positioned reaction wells in adjacent rows have identical processing times. The Microtiter ® plates are incrementally advanced along a processing line which includes an incubator. In this way, each row in the plate is exposed to the same sections of the incubator for the same length of time as every other row so that "edge effect" is minimized.

The processing line has processing stations for simultaneously washing and for simultaneously adding reagents to each reaction well in a row. The processing stations are movable with respect to the incubator so that incubation times can be varied according to the type of assay being run.

A control system controls the instrument, permitting variation in incubation times, quantity of reagent added, dilutions, and other processing steps.

The instrument has a photodensitometer at the end of the processing line to determine the optical densities of fluid in the reaction wells to determine whether the patient samples are positive or negative. Various filters may be used with the photodensitometer, as selected by the control system according to the type of assay being run.

In a preferred embodiment, the instrument has two processing lines which allow two different tests to be performed simultaneously.

BRIEF DESCRIPTION OF THE DRAWINGS

FIG. 5 is a partial sectional, elevational view, taken generally along line 5—5 of FIG. 4.

FIG. 6 is an enlarged sectional view of a bottom corner of the test tube rack and loading station switch key pad.

FIG. 7 is an enlarged sectional view of a bottom corner of the test tube rack in position on the instrument taken generally along line 7—7 of FIG. 4.

FIG. 8 is an isometric view of a conventional Microtiter ® plate with one of the reaction well strips removed.

FIG. 9 is an enlarged isometric view of a position indicating the feedback mechanism.

FIG. 10 is an enlarged partial sectional view of the Microtiter ® plate shown in FIG. 8.

FIG. 11 is an enlarged perspective view of an automatic pipette and associated pipette charging system.

FIG. 12 is an enlarged partial sectional view of a patient sample test tube containing patient sample with the tip of the pipette therein.

FIG. 13 is an isometric view of one of two identical processing stations.

FIG. 14 is an enlarged sectional elevational view taken along line 14—14 of FIG. 13.

FIG. 15 is an enlarged sectional elevational view taken along line 15—15 of FIG. 13.

FIG. 16 is a schematic representation of an optical system used in a photodensitometer portion of the present invention.

FIG. 17 is a schematic representation of a portion of the photodensitometer.

BEST MODE FOR CARRYING OUT THE INVENTION

Figure 1:
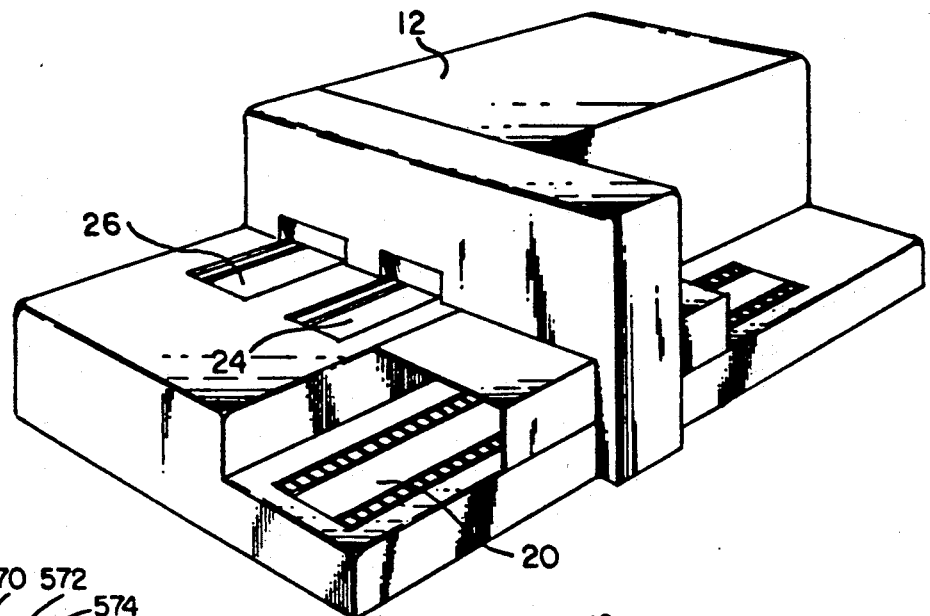
FIG. 1 is an isometric view of an automated patient sample analysis instrument in accordance with the present invention.
Figure 2:
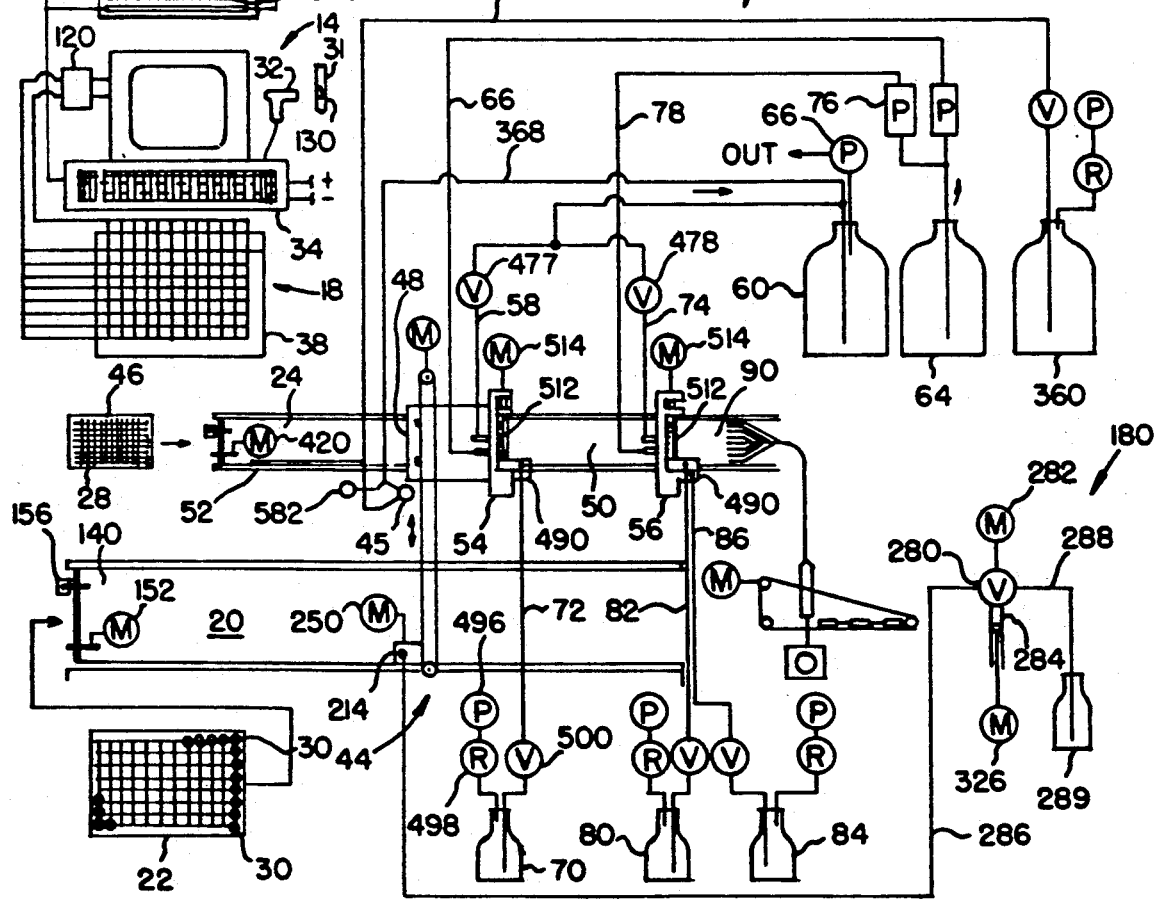
FIG. 2 is a schematic representation of the instrument shown in FIG. 1, including a loading station, a computer, and an electronic service module which interfaces the instrument with a conventional programmable computer.

An automated patient sample analysis instrument in accordance with the present invention is generally indicated in a schematic representation (reference numeral 10 in FIG. 2). The instrument has four main components, consisting of a main instrument 12, as seen in FIG. 1, a computer control system 14, shown in FIG. 2, an electronic service module 16, and a test tube rack load station 18. The instrument has the ability to automatically process two different ELISA-type tests from one set of patient samples. The instrument virtually eliminates irreproducible ELISA test results due to human error. The instrument also speeds the testing procedure, reduces operator tedium, and decreases variability over the entire testing process.

Overview

A brief overview of the instrument's operation will facilitate understanding of the detailed description below. Referring to FIGS. 1 and 2, the main instrument 12 has a test tube rack conveyor 20 which advances a test tube rack 22 into the main instrument 12. The main instrument also has two Microtiter ® plate processing lines 24, 26 which accept conventional Microtiter ® plates. One Microtiter ® plate 28 is illustrated in FIG. 2 on one of the Microtiter ® plate processing lines 24, which is also shown in FIG. 2. It is to be understood that the Microtiter ® processing line 26 is identical to processing line 24 and is therefore excluded from schematic representation in FIG. 2.

Figure 18:
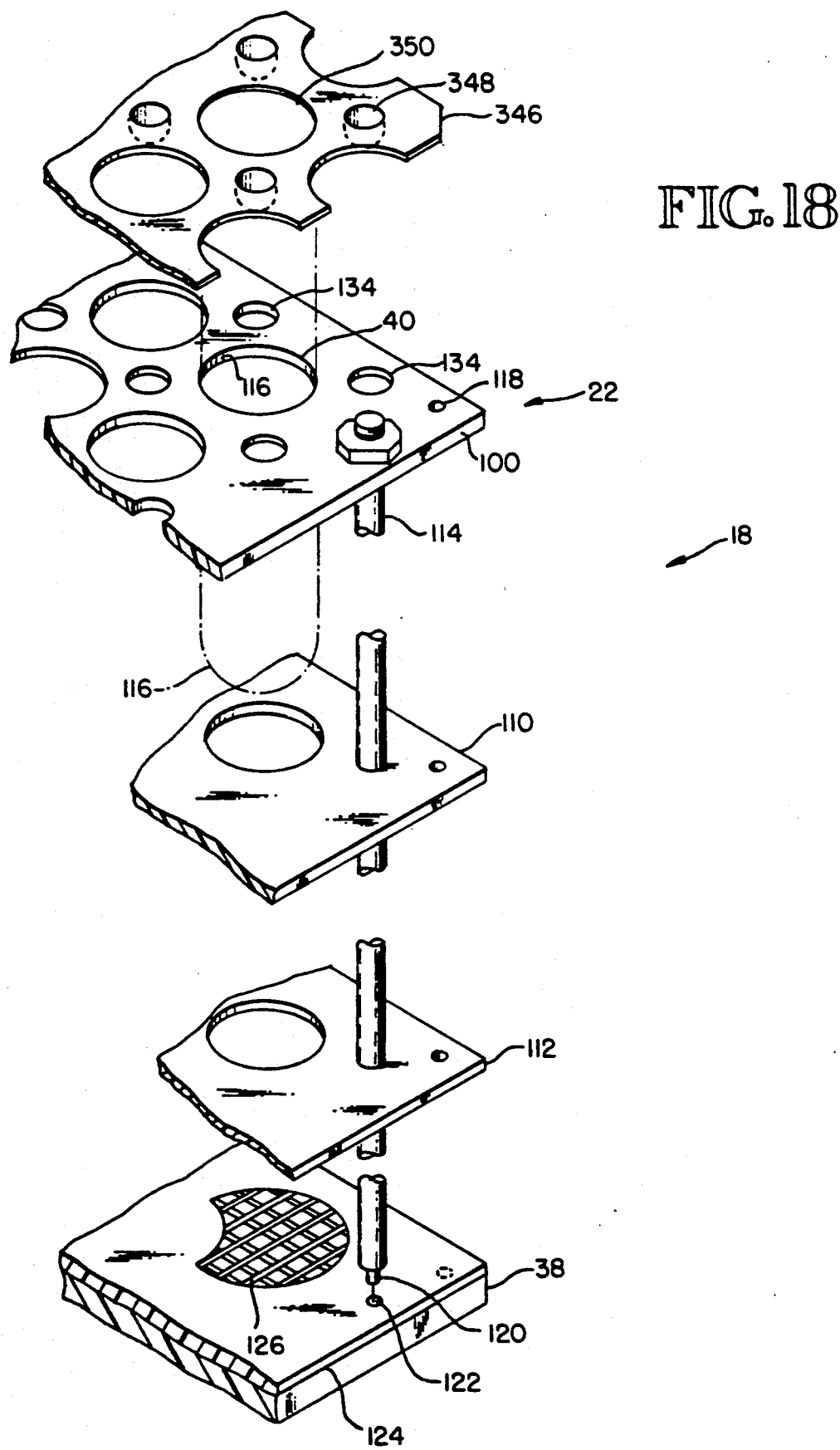
FIG. 18 is an enlarged partial isometric view of the test tube rack, load station, and dilution cup template.

Test tubes 30 containing patient sample (usually sera or plasma) are first identified by patient name or identification number to the instrument 10 by a bar code reader 32 connected to the computer control system 14 or are manually entered into the computer control system through a keyboard 34. Either the technician or the computer control system selects a desired receptacle location in the test tube rack 22, and the computer system 14 then instructs the technician, by way of a display 36, to insert the identified test tube 31 (FIG. 2) into the desired receptacle location in the test tube rack. During this process, the test tube rack is positioned on a loading station pad 38, as shown in FIG. 18, which senses the receipt of the identified test tube in the desired receptacle location.

In the preferred embodiment, the computer control system selects the desired receptacle locations by assigning identified test tubes to a matrix location in the test tube rack in a regular pattern with which the technician is familiar. For example, rows and columns in a Microtiter ® plate are typically designated as columns A-H and rows 1-12. The first position in a Microtiter ® plate is therefore A,1. The test tube rack 22 is arranged with test tube receptacles 40 in identical matrix positions, thus, the computer control system 14 preselects the desired locations by incrementing row and column coordinates to fill the test tube rack, usually in a logical row-by-row progression.

The operator/technician receives a visual and audible verification on the display 36 that the identified test tube has indeed been received in the selected or preselected desired receptacle location. This can be achieved by programming the computer system to display a character such as "O" for the selected or preselected desired location and an "X" for locations which have already received test tubes. When the identified test tube is inserted into the receptacle at the desired location, the O character becomes an X character and the computer system preferably generates an audible verification tone. Once test tubes have been received in the test tube rack 22, they should not be removed by the operator/technician so that their coordinate location will remain unchanged throughout the entire testing process.

Should the tube be inserted into a receptacle other than at the desired location, the O character will not change to an X character, nor will an audible tone be generated. In addition, the computer control system is programmed to prevent the identification of a subsequent test tube until the previously identified test tube 31 has been sensed as received in the receptacle at the desired location in the test tube rack. In this way, an operator/ technician cannot proceed with further test tube identifications until the identified test tube is properly positioned in the test tube rack. Once the test tube rack has been fully loaded with identified test tubes, the test tube rack is transferred to the test tube rack conveyor 20 on the main instrument 12.

The test tube rack conveyor 20 advances the test tube rack 22 until the first row of test tubes is sensed as being directly beneath a transfer station, generally indicated at numeral 44. The transfer station transfers (and, if necessary, dilutes) patient sample from the identified test tubes 30 into corresponding reaction wells 46 of the Microtiter ® plate 28. After one row of patient samples from the identified test tubes 30 has been automatically transferred to corresponding reaction wells 46 in the Microtiter ® plate 28, the first row of the Microtiter ® plate is advanced in a processing direction above a first end 48 of an elongated incubation surface 50. The incubation surface has a second end 51 displaced from the first end. Transferring patient samples from one row of test tubes to one row of reaction wells (including dilution, if necessary) takes less than four minutes. Therefore, the Microtiter ® plate processing line 24 has a Microtiter ® plate conveyor 52 which advances the Microtiter ® plate in increments of one center-to-center reaction well row width every four minutes.

After a patient sample (or dilution thereof) has been transferred to a corresponding reaction well, the tip of the transferring station is washed at a wash station 45, as will be described more fully below.

The Microtiter ® plate processing line 24 has first and second processing stations 54, 56 which are spaced relative to one another and relative to the first end 48 of the elongated incubation surface 50 to define first and second incubation periods. The processing stations are movable relative to one another in increments equal to a row width (the distance traversed by the Microtiter ® plate conveyor 52 every four minutes) so as to provide means for varying the incubation periods to accommodate the particular test being run.

The first processing station performs a number of functions. The reaction wells 46 are initially coated with a first reactant which is capable of binding with an analyte suspected of being present in the patient samples. After the patient samples and first reactant have incubated during the first incubation period (defined by the time required to travel the distance between the first end 48 of the elongated incubation surface 50 and the position of the first processing station 54), the processing station removes simultaneously the patient sample and any unbound analyte from each reaction well in a row. The first processing station then thoroughly washes simultaneously each of the reaction wells in the row and then sequentially adds a predetermined quantity of a reporter/ second reactant conjugate to each reaction well in the row.

To accomplish the wash, the patient sample and unbound analyte are first removed from the reaction wells in the row through an aspiration line 58 which empties into a biohazard container 60 containing a bleach solution. The biohazard container is maintained at a slightly negative (referred to as "atmospheric") pressure by a vacuum pump 62.

Each reaction well in the row is then washed with a wash solution contained in a wash solution bottle 64 through wash line 66 by way of a solenoid-operated, pulsating liquid pump 68. Wash solution is aspirated from the reaction wells as previously described.

The first processing station then sequentially adds the reporter/second reacted conjugate from a conjugate bottle 70 through a conjugate line 72. The aspiration/ washing/conjugate addition sequence can occur in less than one minute. The conjugate reagent is then incubated during the second incubation period, which is defined by the time required to travel the distance between the first processing station 54 and the second processing station 56.

When the first row of reaction wells 46 arrives at the position occupied by the second processing station 56, a sequence of events commences similar to the sequence of events which occurred at the first processing station. Unbound, reporter/second reactant conjugate is simultaneously removed from each reaction well in the row through aspiration line 74 and is received in biohazard container 60. Each microwell in the row is then simultaneously washed with wash solution from wash solution bottle 64 by way of a second solenoid-operated liquid pump 76 through a second wash line 78. A predetermined quantity of a chromogenic substrate is then sequentially added to each well in the row from a chromogenic substrate bottle 80 through a substrate line 82. Removal of unbound, reporter/second reactant conjugate from each reaction well in the row, washing each reaction well in the row, and adding the predetermined quantity of chromogenic substrate to each reaction well in the row can be achieved in less than ten seconds.

After a relatively short third incubation, a stop solution contained in stop solution bottle 84 is sequentially delivered to each reaction well in the row through stop solution line 86. Addition of the stop solution can be achieved in less than five seconds.

After the chromogen reagent is added and the Microtiter ® plate allowed to incubate through the third incubation period, a color will develop in proportion to the amount of bound analyte present. Addition of the stop solution at the end of the third incubation period stops all the reactions in the reaction well row.

A movable, vertical photodensitometer 88 is located at an exit end 90 of the Microtiter ® plate processing line 24. The photodensitometer determines the optical density of the solution in each reaction well of a row at specific wavelengths. For some assays, e.g., LAV, this information is then compared by the computer control system 14 to absorbance values for positive and negative controls which have been included in the Microtiter ® assay. Based on this comparison, the computer control system will indicate on the display 36 the test results for each patient sample contained in the identified test tubes 30 as being either positive or negative. For some assays, if positive results occur for any patient sample, the test must be repeated for that individual sample.

As will be apparent to those skilled in the art, once the test tube rack 22 has been transferred to the test tube rack conveyor 20, a second set of patient sample test tubes can be identified and positioned in appropriate receptacles in a second test tube rack (not shown) positioned on the now vacant loading station pad 38.

It is important to note that once the patient sample test tubes 30 have been identified to the computer control system 14 and the fully loaded test tube rack 22 transferred to the test tube rack conveyor 20, further human intervention is not necessary to complete the test. Therefore, the possibility of test result inaccuracies due to human error is virtually eliminated. Furthermore, the maximum variation in reaction time between any two patient samples (front-to-back error) is four minutes, a variation which is considered to be insignificant. Further yet, parallel/serial processing of reaction well rows minimizes temperature and other row-to-row processing variations as each row is subjected to the same processing conditions.

DETAILED DESCRIPTION USING ELISA TEST FOR LAV ANTIBODY

The following detailed description uses an ELISA test for the lymphadenopathy-associated virus (LAV) antibody manufactured by Genetic Systems, Inc., Seattle, Wash., and sold under the trademark LAV EIA ™. The Genetic Systems LAV EIA ™ test is manufactured from virus propagated in a CEM cell line. The infected cell line is cultured and the virus is purified by centrifugation. The viral concentrate is disrupted and inactivated using a chaotropic agent and heat prior to coating the Microtiter ® plate reaction wells. The following detailed description also describes use of the instrument 10 with an ELISA test for detection of hepatitis B surface antigen manufactured by Connaught Laboratories Ltd., Willowdale, Ontario, Canada.

It is to be understood that these examples are for the purpose of illustration only. The automated patient sample analysis instrument 10 is highly versatile and can be adapted to perform a number of other ELISA-type tests.

The preferred embodiment has been developed to independently process Microtiter ® plates prepared for detection of the LAV antibody and the hepatitis B surface antigen. These two tests are particularly important in blood screening programs for hospitals and other institutions. As will be more clearly understood from the description which follows, the apparatus can be adjusted and modified to run a variety of other tests and tests which have yet to be developed.

As previously stated, the automated patient sample analysis instrument 10 has four main components: the main instrument 12, the computer control system 14, the electronic service module 16, and the test tube rack load station 18. The computer control system serves to coordinate various actions of the main instrument 12 and serves as the memory for the patient sample locations. The electronic service module 16 converts the computer control system's digital signals into analog drive signals for various motors and systems in the main instrument 12. The electronic service module also converts analog signals from feedback sensors and other detectors on the main instrument into digital signals for use by the computer control system. The test tube rack load station 18 provides a sensory device for confirming receipt of identified test tubes in the proper test tube rack receptacles.

A more detailed view of the test tube rack load station 18 is shown in FIG. 18. The test tube rack load station includes the test tube rack 22, which has an upper plate 100, an intermediate plate 110 and a bottom plate 112. The plates are interconnected in a spaced relationship by six vertical support columns 114 spaced around the periphery of the test tube rack 22, with a column at each of the rack's corners. Each plate has a regular matrix array of circular openings 116 which define the test tube receptacles 40. In this preferred embodiment, the receptacles are designed to accommodate 12×75 mm, 13×100 mm, or other standard sized test tubes. The diameter of the receptacles 40 is slightly larger than the diameter of these test tubes to allow relative vertical movement of the test tubes within the receptacles once the test tubes have been received.

One of the vertical columns 114, as shown in FIG. 18, is displaced from the corner position 118. Each vertical column has indexing pins 120 extending therefrom below the bottom plate 112 which are received in corresponding pin holes 122 in the loading station pad 38. The indexing pins 120 are therefore capable of mating with the pin holes 122 only when the test tube rack is oriented in a single direction. The loading station pad 38 is provided with a multi-position membrane switch keypad 124 positioned under the rack when received on the loading station pad with the rack properly oriented using the indexing pins. The keypad has a normally open pressure-sensitive membrane switch 126 located beneath the position of each test tube receptacle 40.

As best seen in FIG. 6, the resilient nature of the membrane switch slightly lifts the test tube 30 from its rest position in the test tube rack 22. The switch is only closed when the technician/operator inserts the test tube into the receptacle and presses the tube downward against the membrane switch with sufficient force to cause switch actuation. This registers the test tube placement and causes the display 36 to indicate that the identified test tube has been received in the correct, desired receptacle. Upon the technician/operator releasing the test tube, the switch 126 will resume its normally open position. This arrangement of membrane switches allows a conventional decoding circuit 128 (see FIG. 1) to be used for inputting the coordinate location of a received test tube to the computer system 14. Other systems could be substituted. For example, optical detectors could be used to determine whether a test tube is resident in the receptacle or not, thus providing continuously updated information as to whether or not a test tube has been inserted or removed.

As previously stated, it is preferred to utilize a bar code reader 32 for entering patient sample information from a bar code label 130 applied to the exterior of each test tube 30 to identify a patient sample, as is presently the practice in many large hospitals and other institutions. Bar code readers are available for a number of personal computers as optional equipment. In the event that a bar code reader is not available or desired, the patient sample information can be typed into the computer system 14 through the keyboard 34. The preferred embodiment uses an IBM-compatible personal computer; however, any computer system having at least 640 kilobytes of random access memory should be sufficient to run the software for the automated patient sample analysis instrument 10. The computer system 14 is also programmed to display special instructions for each individual test to be run. For the LAV EIA tests, two positive controls and three negative controls should be assayed with each Microtiter ® plate or partial Microtiter ® plate. The positive controls contain human serum having anti-LAV immunoglobulin, which is nonreactive for HBsAg and not infectious for LAV (heat-treated). The positive controls establish an acceptable maximum value for total absorbance. The negative controls establish a total absorbance, which, added to a predetermined value, establishes the cutoff value for a positive test result. As shown in FIG. 8, the plate 28 has removable reaction well strips 132 (including a full row of wells) which may be removed if processing of less than ninety-six samples is desired.

The test tube receptacles 40 are spaced on center approximately 0.75 inch apart. The upper plate 100 also includes dilution cup receptacles 134 which are spaced in a regular matrix array having centers approximately 0.75 inch apart but displaced laterally 0.375 inch from the coordinate locations of the test tube receptacles 40. Therefore, the lateral displacement (in both horizontal directions) from the center of a dilution cup receptacle 34 to a test tube receptacle 40 is 0.375 inch.

The test tube rack 22 is advanced from a first end 140 of the test tube rack conveyor 20 by a pair of spaced-apart, endless belts 142. As best seen in FIG. 7, the belts have depressions 144 spaced at intervals of 0.375 inch to correspond to the separation distances of the dilution cup receptacles 134 and test tube receptacles 40. The depressions are adapted to receive the indexing pins 120 to positively position the test tube rack 22 on the test tube rack conveyor.

Figure 4:
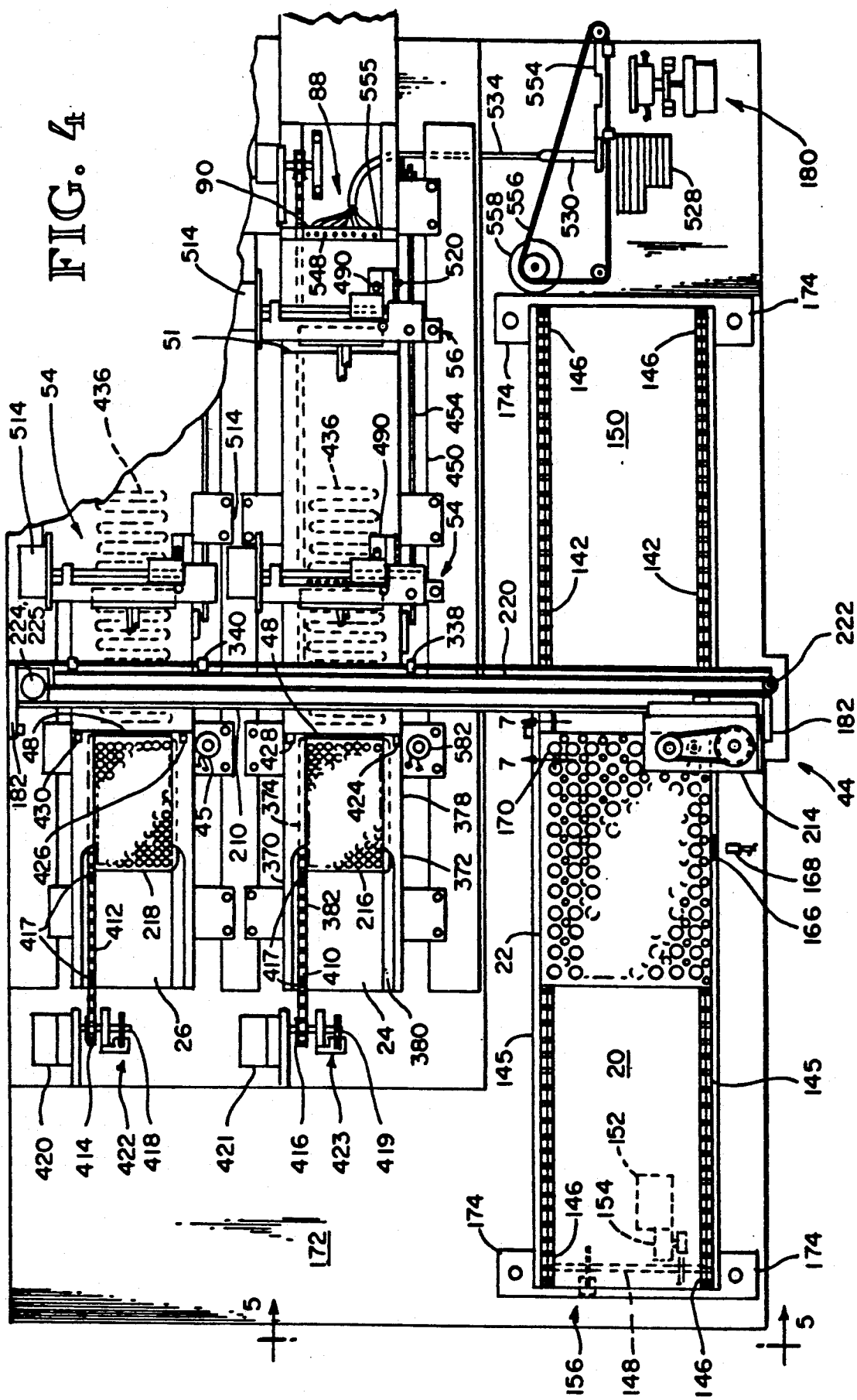
FIG. 4 is a top plan view of the instrument shown in FIG. 1 with a portion of the instrument cut away.

As shown in FIG. 4, the test tube rack 22 is laterally positioned by elongated rods 145 outboard of the belts 142. The belts are each entrained on a pair of spaced-apart drive wheels 146 which are fixedly connected for rotation to the ends of a power-driven shaft 148 and an idler shaft 150. The endless belts 142 are driven in stepped increments of 0.375 inch by a 300 rpm AC motor 152 having a reduction gear 154 which reduces the rotation of the shaft 148 to 8 rpm when the motor 152 is operating at its rated voltage.

The angular speed and rotation of motor 152, and all the other AC motors to be described below, are controlled by a triac circuit in the electronic service module 16. The angular position of the shaft 148 is monitored by a feedback mechanism 156 shown in FIG. 9. The feedback mechanism has a flag wheel 158 having a plurality of flags 164 journaled to the shaft for rotation therewith. A light emitter/detector pair 160 straddles the flag wheel so that openings 162 in the wheel which define the flags can be detected by the light emitter/detector pair. The output of the emitter/detector pair 160 is transmitted to the electronic service module 16, where conventional circuitry counts the number of flag passings with respect to time so that the computer system 14 can control the motion of the endless belts 142.

The flag wheel flags are displaced approximately 0.375 inch at the position of the light emitter/detector pair. In this way, detection of one flag passage indicates that the test tube rack 22 has been advanced one dilution cup center to one test tube center distance.

The computer system 14 is programmed to advance the test tube rack 22 on the test tube rack conveyor 20 until a reflector 166 is detected by a light emitter/ detector pair 168 to indicate that a first row 170 of test tube receptacles 40 is centered below the transfer station 44. If the reflector is not detected within one-half full revolution of the endless belts 142, the computer system indicates that the operator has either not placed the test tube rack on the test tube rack conveyor 20 or has misoriented the rack by 180°.

Figure 3:
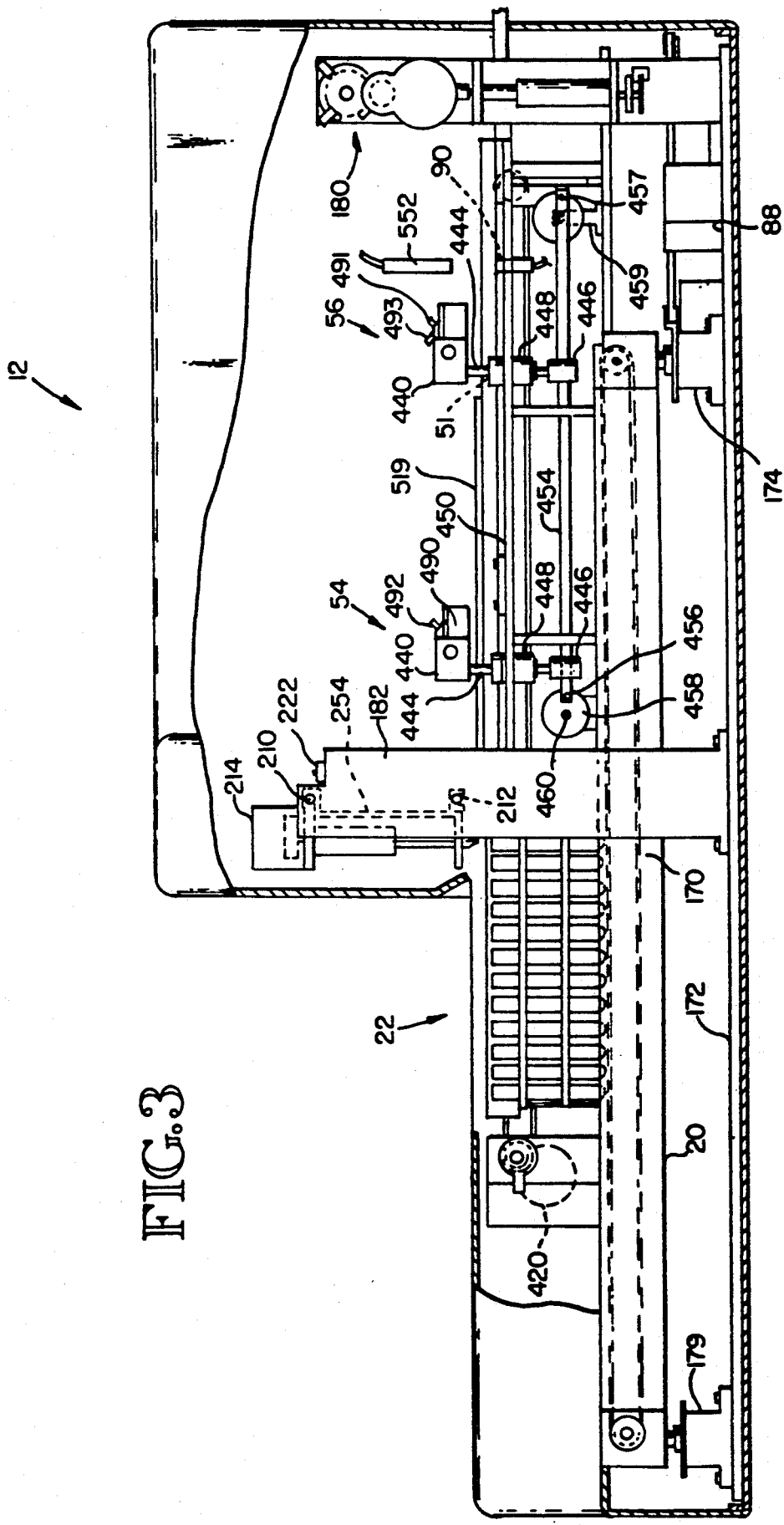
FIG. 3 is a side elevational view of the instrument shown in FIG. 1, with a portion of the instrument cut away and a test tube rack in the instrument.

The test tube conveyor rack 20, as well as other components of the main instrument 12, including the Microtiter ® plate processing lines 24, 25, are supported above a main instrument base 172 by supports 174, as seen in FIGS. 3, 4 and 5.

Parts of the transfer station 44 and an associated diluent control mechanism 180 are shown in detail in FIG. 11. Other details of the transfer station are shown in FIGS. 3 and 5. The transfer station has vertical supports 182 which are connected to the main instrument base 172 laterally outward of the test tube conveyor 20 and Microtiter ® plate processing line 26 and which support two cross rods 210, 212. The cross rods slidably support a moving automatic pipette 214 which draws patient sample from the test tubes 30 in the test tube rack 22 on the conveyor 20, performs necessary dilutions, and transfers the diluted and undiluted patient sample to two separate Microtiter ® plates 28, a ninety-six well plate 216, and a ninety-six well plate 218, respectively. Other sizes of plates may be used, such as forty-eight well plates and the like.

In a LAV antibody assay, the plate 216 is used. In a hepatitis B surface antigen assay, the plate 218 is used. The moving automatic pipette 214 is connected to a looped drive chain 220 having one portion entrained on an idler cogwheel 222 and an opposite portion entrained on a powered drive cogwheel 224. The drive cogwheel is journaled for rotational drive to a conventional DC motor 225 having a quadrature feedback control (two sensors located 90° out of phase with respect to flags to indicate direction of movement). The motor 225 is controlled by a Hewlett-Packard HCTL-1000 DC controller contained in the electronic service module 16. This drive system provides precise lateral positioning of the moving automatic pipette above each test tube receptacle 40 in the positioned test tube rack 22.

The moving automatic pipette 214 has a pipette tube 230 having an open tip end 232 and a diluent receiving end 234. As best shown in FIGS. 5 and 11, the diluent receiving end is retained by a traveling block 236 for vertical movement therewith. The block has a threaded bore which receives a threaded screw 240. The threaded screw has a pulley 244 journaled at one end thereof which is driven by a belt 246 entrained on a motor pulley 248. The motor pulley is driven by a DC motor 250 having a quadrature feedback mechanism 252 and controlled by a Hewlett-Packard HCTL-1000 DC circuit, such as the one previously described. Selected rotation of the screw 240 by the motor 250 causes the traveling block 236 to move up or down to raise or lower the pipette tube 230.

A vertical plate 254 supports an upper horizontal plate 256 and a lower horizontal plate 258. The upper horizontal plate supports the DC motor 250 and rotatably supports the upper end of the threaded screw 240. The lower horizontal plate 258 provides rotational support for the lower end of the threaded screw 240 and sliding support for the pipette tube 230. The traveling block 236 is positioned in sliding engagement with the vertical plate 254 to prevent rotation of the traveling block as the screw is rotated. The traveling block also has a home flag 260 which activates a home detector 262, which is required by Hewlett-Packard in its DC motor control system.

As shown in FIG. 12, the pipette tube open tip end 232 has two electrodes 264 which have free ends 266 positioned at the level of a lower end 268 of the open tip end 232. The electrodes detect the level 270 of patient sample in the test tube 30 into which the pipette tube 230 is inserted and indicate to the controller for the DC motor 250 to stop rotation of the threaded screw 240.

Referring to FIG. 11, the diluent control mechanism 180 has a low dead volume shear valve 280 which is driven by an AC motor 282, similar to AC motor 152. The shear valve provides continuity between either a precision syringe cylinder 284 and a diluent delivery line 286 or the precision syringe cylinder and a diluent supply line 288. The diluent supply line is connected to a diluent supply bottle 280, as shown in FIG. 2. The shear valve 289 has a feedback mechanism 290 including two optical sensors 292, 294 which indicate the position of the valve according to the detected rotational position of openings 296 in a peripheral skirt 298 of the valve.

The precision syringe cylinder 284 has mounted for reciprocal motion therewithin a piston 300. The piston is connected to a plunger rod 310 which is secured to a piston sliding block 312 by a plate 314. Affixed to the plunger rod on an opposite side of the plate is a threaded screw 316 which is threadably received within a nut (not shown). The nut is contained in a sleeve 320 which is fixedly attached at its ends to upper and lower thrust bearings 322, 324 for rotation therewith. The lower thrust bearing 324 is driven by a DC motor 326, similar to the DC motor 250 and the DC motor 225, which drives the drive cogwheel 224, previously described. Quadrature feedback and a home detector 336 are employed, as is required by the Hewlett-Packard HCTL-1000 DC controller circuit.

A horizontal plate 328 is connected to a vertical plate 330. The horizontal plate supports the DC motor 326 and associated quadrature feedback mechanism, a belt drive system 332, and the sleeve and thrust bearing assembly 320, 322, 324. The piston sliding block 312 is positioned in sliding engagement with the vertical plate 330 to prevent rotation of the piston 300 within the precision syringe cylinder 284 as the piston reciprocates. The piston sliding block 312 also has a flag 334 which interrupts the light beam in the home detector 336 to indicate the maximum upward travel of the piston 300.

The vertical plate 254 on the moving automatic pipette 214 is also provided with a flag (not shown) which interacts with a first column indicating detector 338 for the AIDS antibody processing line 24 and a first column indicating detector 340 for the hepatitis B surface antigen processing line 26. These detectors indicate the position of the first column of wells in each plate 216, 218, as shown in FIG. 4. A home detector 342 is also provided. These detectors are mounted on a horizontal channel 344 which is mounted between the vertical supports 182.

When running both the LAV and hepatitis B assays, the computer control system 14 is programmed to operated the transfer station 44 in the following manner. The pipette tube 230 is first charged with diluent from diluent supply line 288 by the diluent control mechanism 180. The diluent control mechanism then draws a small bubble of air into the pipette 230 through the pipette tube open tip end 232 so as to form a small air gap between diluent in the pipette tube 230 and any patient sample or diluted patient sample to be drawn thereafter. This air gap serves to isolate the drawn fluid sample or diluted fluid sample from the diluent column thereabove.

The computer control system 14 then instructs the motor 225, which drives cogwheel 244, to laterally position the pipette tube 230 above the first patient sample (positive and negative controls are processed first under instruction from the computer control system). The pipette tube 230 descends by operation of DC motor 250 until the patient sample level 270 is reached, as indicated by the electrodes 264. Five microliters of patient sample are then drawn to the pipette and the pipette is raised to clear the tops of the test tubes, as shown in FIG. 5.

A first dilution is prepared by moving the pipette tube 230 laterally to position the tube over a dilution cup 348 located adjacent to the test tube from which the sample was drawn and dispensing all of the drawn patient sample into the dilution cup with 95 microliters of diluent, metered and dispensed by the diluent control mechanism into the dilution cup.

One preferred method for providing dilution cups is shown in FIG. 18. A disposable dilution cup template 346 is positioned above the test tube rack 22 and has dilution cups 348 positioned to be received in the dilution cup receptacles 134 in the rack upper plate 100. The template also has openings 350 to permit uninhibited insertion of test tubes into the test tube receptacles 40 therebelow. If this style of dilution cup arrangement is used, the patient sample and diluent forming the first dilution are dispensed into the dilution well 348 immediately adjacent to the corresponding patient sample test tube 30. The test tube rack 22 and moving automatic pipette 214 are driven appropriately by the AC motor 152 and DC motor 225, respectively, to position the open tip end 232 of the pipette tube above the correct dilution cup.

The diluent control mechanism 180 then draws another air bubble into the pipette tube 230 prior to drawing five microliters of the first dilution from the dilution cup into the pipette tube. The moving automatic pipette 214 then moves the pipette tube 230 laterally into position above the corresponding reaction well 46 in the plate 216, as indicated by the first column-indicating detector 338 and the quadrature feedback device on the DC motor 225, which drives cogwheel 224. As previously noted, the plate 216 is used for the LAV assay.

The five microliters of first dilution are dispensed into this corresponding reaction well 46 with an additional 95 microliters of diluent to form a second dilution in the reaction well of approximately one part patient sample to 400 parts diluent. The pipette tube 230 is then moved laterally for washing of the pipette tip end 232 at tip wash station 45. As shown in FIG. 2, tip wash solution is supplied from a tip wash solution bottle 360 to the tip wash station 45 through a tip wash solution line 362. The tip wash solution bottle is pressurized by a regulated air pump 364. The wash solution flow is controlled by a valve 366, with an open time controlled by the computer control system 14. The tip wash station is aspirated by a tip wash station aspiration line 368 which delivers the aspirated wash solution into the biohazard container 60. During the tip washing process, the pipette tube 230 is flushed with diluent by the diluent control mechanism 180.

After the pipette tip washing sequence is completed, an air bubble is again drawn into the pipette tube 230 and the pipette tube is moved laterally into position once again over the test tube 30 in the rack 22 having the patient sample to draw approximately 220 microliters of the same patient sample into the pipette tube. The moving automatic pipette tube 214 then moves the pipette tube 230 laterally into position above the corresponding reaction well 46 in the plate 218, as indicated by the first column-indicating detector 340 and the quadrature feedback DC motor which drives the drive cogwheel 224. The undiluted patient sample is delivered to the corresponding reaction well. It has been found that although 220 microliters of patient sample are drawn into the pipette tube, approximately 20 microliters are left on the inside wall of the pipette and must be flushed out in a subsequent pipette tip washing sequence, as previously described. As previously noted, the plate 218 is used for the hepatitis B antigen assay.

The above sequence is repeated until the first row in each of the plates 216, 218 has been filled with the appropriate amount of diluted patient sample and undiluted patient sample, respectively. At the speed with which the instrument operates, both rows can be filled in less than four minutes. The plates are therefore advanced along the processing lines 24, 26, respectively, in increments equal to the center-to-center reaction well spacing between adjacent wells every four minutes. This allows sufficient time to fill each successive row before the rows are advanced by the next increment.

As shown in FIG. 4, each plate processing line 24, 26 has two guide tracks 370, 372, each having a pair of opposed, longitudinally extending side slots 374, 378 adapted to receive laterally outward extending side flanges 378 at the base of the plates 216, 218. Each guide track has upwardly open portions 380, 382, respectively, at the beginning of the track which are cut away to reveal the slots 374, 378 so that the plates can be inserted into the slots from above. Each plate processing line 24, 26 includes an endless belt 410, 412, respectively, which is rotated by pulleys 414, 416, respectively, to move the plates in a processing direction. The belts 410, 412 are fitted with drive dogs 417 positioned one plate length apart to positively position the plates with respect to the belts. The pulleys 414, 416 have peripheral teeth to prevent the belts from slipping thereon.

The pulleys are fixed to powered shafts 418 and 419, which are rotatably driven by AC drive motors 420 and 421, similar to AC drive motor 152. Rotation of the drive shafts 418 and 419 is monitored by feedback mechanisms 422 and 423, similar to feedback mechanism 156. The arc length spacing between the flagwheel flags at the detector is equal to the row-to-row center spacing on the plates. Therefore, detection of a flag by the sensor indicates that the plate has been advanced one row. Once moved past the open track portions 380, 382 on the guide tracks 370, 372, the plates 216, 218 can be removed only by reversing the direction of endless belts 410, 412 to reposition the plates at the open track portions or to rotate until they exit at the far end.

Optical emitters 424, 426 emit beams which are detected by optical detectors 428, 430. The emitters and detectors are positioned so that interruption of the emitted light beams by the plates 216, 218 indicates the presence of the first row in each plate at a position to be below the pipette tube 230 upon appropriate lateral movement of the moving automatic pipette 214.

After the diluted patient sample has been added to one row of the plate 216 and after undiluted patient sample has been added to one row of the plate 218, the plates are both advanced generally simultaneously by the endless belts 410, 412 one increment into the first end 48 of the elongated incubation surface 50 for the corresponding plate processing line 24, 26, as previously described. It is noted that this incremental movement positions the next row of wells for filling by the pipette tube.

The incubation surfaces 50 are each constructed from a 0.50-inch thick, elongated aluminum plate. A silicon rubber resistive heater 436 is bonded to the underside of the elongated incubation surface. The heater is thermostatically controlled by conventional circuitry in the electronic service module 16 according to preprogrammed instructions from the computer control system 14. For these tests, the thermostats are set to maintain a temperature of approximately 37° C. The heater is proportionally driven such that the greater the temperature differential which exists between the thermostatically measured temperature and the desired temperature, the longer the heater will remain on.

The first incubation periods for each plate processing lines 24, 26 are determined by the time required for the plates to incrementally move the distance between the first end 48 of the elongated incubation surfaces 50 and the first processing stations 54. For the LAV antibody assay and the hepatitis B surface antigen assay, the first incubation period for each processing line should be one hour. As previously stated, the first and second processing stations 54, 56 are movable with respect to one another and with respect to the incubation surfaces in order to select the length of the incubation period desired. To establish the one-hour incubation period, the first processing stations should be positioned at a sufficient distance from the first ends 48 so that each reaction well row is provided fifteen four-minute increments for incubation. As each row reaches the end of the incubation period, that row will be under the position of the first processing station.

The first and second processing stations 54, 56 are substantially identical in construction. As best seen in FIGS. 3, 5 and 13, the first and second processing stations are movable in a vertical plane along the processing line. Each processing station has a frame 440 which is supported by vertical stanchions 444, the ends of which are received in sliding blocks 446. The stanchions pass through bushing blocks 448, which are slidably engaged with horizontal flanges 450, seen in FIG. 4. The bushing blocks 448 have bushings through which the stanchions may reciprocate. The flanges are provided with drilled location holes or detents at spaced intervals corresponding to the center-to-center spacing between plate reaction well rows for positioning of the bushing blocks relative thereto. By these means, the positioning of the processing stations are variable.

The sliding blocks 446 are each slidably mounted on a connecting rod 454, best seen in FIG. 3, having an end 456 eccentrically mounted to the periphery of a crank wheel 458, and another end 457 eccentrically mounted to a second crank wheel 459. The crank wheels are rotated by a drive shaft 460, which is driven by an AC drive motor 462 similar to AC drive motor 152. The crank wheels 458, 459 can be rotated to raise and lower the connecting rod 454, and hence simultaneously move the first and second processing stations 54, 56, mounted thereto by the sliding blocks 446, between a raised and a lowered position. One of the crank wheels 458 has two flags 464 (see FIG. 5) similar to the peripheral skirt 298 on the feedback mechanism 290 of the low dead volume shear valve 280. The flags 464 are positioned approximately 80° apart. Thus, the detectors associated with the flags 464 instruct the computer control system 14 as to when the sliding blocks 464, and therefore first and second processing stations 54 and 56, are in a fully raised position or fully lowered position.

As best seen in FIG. 14, each processing station has an aspiration manifold 466 having eight vertical aspiration tubes. Each aspiration tube has an outlet 470, approximately at the center of the manifold, to reduce pressure differences between tubes due to laminar flow. Each aspiration tube also has a fluid inlet 472 positioned to be above the level of the top 474 of the reaction wells when the processing stations are in the raised position. The length of vertical travel of the processing stations is sufficient to place the fluid inlet 472 adjacent to the transparent well bottom 476 when the processing stations are in the lowered position.

A partial vacuum is formed in the aspiration manifold 466 by aspiration lines 58, 74. A partial vacuum is established, as previously discussed, by vacuum pump 62. The vacuum pump 62 produces a relatively weak vacuum. The aspiration lines 58, 74 can be independently controlled by the computer control system 14 through conventional solenoid-operated valves 477, 478, respectively.

Size 18-gauge needles are preferably used for the aspiration tubes. The interior diameter of the aspiration tubes is approximately 0.033 inch. The rate at which the AC drive motor 462 rotates is controlled so that the aspiration tubes are lowered into the reaction wells at a rate which is equal to the rate at which the fluid level is falling in the wells. Thus, the fluid inlet 472 always remains slightly ahead of the falling liquid level. This causes a meniscus 480, which is formed by surface tension in the liquid, to scrub the walls 482 of the reaction well dry of any remaining fluid droplets as the liquid level falls. The vertical travel time of the aspiration tubes is approximately one second. After the patient sample and unbound analyte (or diluted patient and unbound analyte) have been removed by the aspiration tubes, wash tubes 484 vigorously wash the aspiration tubes and the reaction wells with high pressure jets of wash solution from wash line 66 for the first processing station and from second wash line 78 for the second processing station.

Each processing station has a wash manifold 486 which is charged with a high-pressure stream of wash solution by the solenoid-operated liquid pump 68 or second solenoid-operated liquid pump 76. A suitable pump is manufactured by Valcor Engineering Corp., Springfield, N.J. Each wash manifold has eight 19-gauge needle sized wash tubes 484 having an interior diameter of approximately 0.027 inch. The wash tubes are angled toward the aspiration tubes at a relative angle of approximately 15° and have fluid outlets 488 positioned to direct a high-pressure stream of wash solution at the adjacent aspiration tube. The wash solution impinges upon the aspiration tube to cleanse the aspiration tube and disperse the wash solution into the corresponding reaction well positioned therebelow. Thus, contrary to the prior art, wash solution injected into the reaction wells can be immediately aspirated because it is not necessary to wait for diffusion to cleanse the wells. The spray of the dispersed wash solution provides an agitated scrubbing action and substantially reduces the amount of time required to process a row of wells and the corresponding aspiration tube.

To achieve the desired pressure, the solenoid operated pumps 68, 76 have a displacement of approximately 1 milliliter per stroke, with a stroke period of approximately 100-200 milliseconds. Three strokes are used per wash. It has been found that displacement of this quantity of fluid in this time period while using wash tubes having an interior diameter of 0.027 inch provides satisfactory scrubbing action. Three wash and aspiration cycles are completed for the LAV test first processing line 24. Five such cycles are used for the hepatitis B test second processing line 26. The computer control system 14 is appropriately programmed for the number of wash cycles recommended by the test manufacturer. It is preferred to inject three blasts of washing fluid, as previously described, prior to each aspiration after the initial aspiration. The wash tube angle, in conjunction with three short, high-pressure jets of washing solution, is believed to have provided a superior cleansing action in the reaction wells. The final aspiration, however, should last several seconds to remove any remaining wash solution droplets.

Each of the first and second processing stations 54, 56 includes a size 21-gauge needle 492, 493 having an interior diameter of 0.020 inch mounted in a laterally traveling block 490, 491. After the first wash cycle has been completed at the first processing station 54, the needle 492 separately dispenses a reporter/second reactant conjugate (hereinafter "conjugate") to each reaction well in the row of wells therebelow. In the case of the LAV test, the conjugate is a peroxidase-labeled goat anti-human immunoglobulin which will bind to the antibody-antigen complex, if present. In the case of the hepatitis B test, the conjugate is a chimpanzee anti-HB$_s$ peroxidase conjugate. The needle has a fluid-dispensing end 494 which is sufficiently spaced above the reaction well top 474 so as to avoid interference therewith when the process stations 54, 56 are moved to the lower position. The needle is angled sufficiently and the conjugate is delivered under sufficient pressure so that the conjugate is delivered into the well without any dripping outside the reaction wells.

As previously discussed, the conjugates are contained in a conjugate bottle 70 which is pressurized by an air pump 496 and regulated by a regulator 498. Fluid flow is regulated by a time-controlled conjugate valve 500 in what is conventionally known as a "pressure-gated delivery system." In this system, the pump runs continuously and the regulator maintains a controlled pressure in the bottle. The valve 500 is a pinch valve which is opened for a relatively short period of time. Thus pressure in the bottle is not substantially changed. Conjugate delivery is therefore precisely measured.

Traveling block 490 has a laterally extending, interiorly threaded portion 510 which receives a threaded screw 512 (see FIG. 14) which extends laterally across the full width of the processing station. The threaded screw is rotated by an AC triac circuit-controlled drive motor 514 (see FIG. 4) similar to motor 152. The position of the traveling block is monitored by a light emitter/detector pair 516. The light beam established therebetween is intercepted by a plurality of flags 518. One flag is positioned at the location of each column of reaction wells in the plates 216, 218. The computer control system 14 looks for the presence of a flag in the light beam as the signal to stop the traveling block 490 and to dispense conjugate into the reaction wells. Using this system, conjugate can be added to a row of eight reaction wells in approximately ten seconds. The traveling block is also provided with a home detector, which is not shown. The home detector is positioned to indicate that the traveling block is in a position, adjacent to the edge of the plate, to allow the lowering of the processing stations 54, 56 without interference from the needles 492, 493.

When running the LAV test, approximately 100 microliters of conjugate are added at the first processing station to each reaction well, whether it contains a patient specimen or a control. When running the hepatitis test, approximately 200 microliters of conjugate are added at the first processing to the reaction wells.

After the conjugate has been added to each reaction well in a row, the endless belts 410, 412 advance that row beyond the first processing station 54, and the second incubation period is defined by the time the row takes to travel the distance between the first processing station 54 and the second processing station 56. For both the LAV and the hepatitis test, the incubation period is one hour, which corresponds to fifteen row increments. The tracks 372, 374 may be provided with sectioned Plexiglas® covers 519 (see FIG. 3) positioned above the plates 216, 218 to cover the portions of the elongated incubation surface 50 which are not occupied by processing stations.

As shown in FIG. 4, the second end 51 of the elongated incubation surface 50 is adjacent to the second processing station 56. In this way, the third incubation period occurs at room temperature. The length of the incubation surface should be selected according to the incubation periods specified by the test manufacturer.

At the end of the second incubation period (after the plates 216, 218 have advanced fifteen increments), the first row of each plate will be in position below the corresponding second processing stations 56. At these stations, the aspiration and wash procedures are completed as previously described for the end of the first incubation period. The second vertical 21-gauge needle 493 then dispenses the chromogenic substrate (chromogen reagent) from chromogenic substrate bottle 80 into each reaction well. The reaction well rows are thus advanced into the third incubation period.

The traveling block 491 of the second processing station 56 carries a third 21-gauge needle 520 inserted in an aperture 522 (see FIGS. 4 and 15) for dispensing the stop solution. Aperture 522 is one of a plurality of parallel apertures. These apertures are oriented transverse to the second 21-gauge needle 493 in the second processing station 56. As shown in FIGS. 14 and 15, fluid-dispensing end positions 527 of the third 21-gauge needle, when positioned in the various apertures 522, are collinear with the column of reaction wells serviced by the second 19-gauge needle 92. However, the fluid-dispensing end portions 527 of the third 21-gauge needle 520 are spaced apart so as to be displaced 4, 5, 6 or 7 row width increments from the second 21-gauge needle fluid-dispensing end 494, depending into which aperture 522 the third needle is inserted. This distance defines the duration of the third incubation period for the chromogenic substrate.

The third needle is connected to the stop solution bottle 84 by way of stop solution line 86. The pressure therein is regulated in the same manner as for the chromogenic substrate bottle 80 and conjugate bottle 70.

For both the LAV and hepatitis tests, the stop solution is added to the reaction wells approximately thirty minutes (8 increments) after the chromogenic substrate has been added. During the third incubation period for the chromogenic substrate, a color will develop in proportion to the amount of analyte which has bound to the first reactant. The stop solution stops the reaction and results in a further color change.

As previously stated, the vertical photodensitometer 88 is located at the second end 90 of the elongated incubation surface 50. The photodensitometer is movable in the processing direction in a manner similar to that described for the first and second processing stations 54, 56, as previously described. A schematic representation of the photodensitometer is shown in FIGS. 16 and 17. It is preferred to add approximately 100 microliters of chromogenic substrate at the end of the second incubation period and 50–100 microliters of stop solution at the end of the third incubation period so that all the reaction wells in the plate contain approximately 150–200 microliters of solution. This causes a fluid meniscus to exist in each reaction well substantially at the same location.

As shown in FIG. 16, the photodensitometer has a light source 528, preferably using a quartz halogen lamp. A conventional lens system 530 focuses the image of the light source 528 on a light guide bundle 532. The light guide bundle in FIG. 16 is shown as containing only eight fibers. The system actually has sixteen fibers, with eight fibers going to each of the first and second processing lines 24, 26. The individual light guide fibers 534 terminate in a polished end 536. The light beam emanating therefrom passes through a first aperture 538 which rejects stray light. The light beam then passes through a focusing lens 540, which causes the beam to converge and have a narrowest portion 542 substantially at the center of the fluid meniscus 480 formed in the reaction well. A second aperture 544 further restricts the light beam so that stray light does not enter through the transparent bottom 476 of the reaction well.

The optical axis defined by the focusing lens 540 is also substantially perpendicular to the fluid meniscus at the center thereof. It has been found that by focusing a light beam so that the optical axis is substantially perpendicular to the meniscus and so that the narrowest part of the light beam intersects the meniscus substantially at its center, refraction caused by the meniscus curvature is minimized. Refraction is particularly undesirable in absorbance-type measurements because refracted light beams may not enter a detector and therefore may be incorrectly interpreted as having been absorbed by the fluid sample. In the present invention, the detector 546 is placed directly above the open top of the reaction well and has a diameter approximately twice that of the expected diameter of the light beam at the detector.

The meniscus focusing system is contained in a lower optical housing 548 beneath the elongated incubation surface 50. Eight apertures 550 are formed therein to allow the light beam to pass therethrough. The detectors 546 are housed in an upper unit 552, which, as best seen in FIG. 3, is sufficiently spaced from the elongated incubation surface 50 to allow a plate to advance therebetween.

The photodensitometer also has a plurality of filters 554 having different transmission characteristics. Filters are mounted on a revolving belt driven by an AC triac-controlled drive motor 558 similar to drive motor 152. The drive motor 558 utilizes a feedback mechanism similar to feedback mechanism 156 to permit the computer control system 14 to select the appropriate filters for the tests being conducted.

The electronic service module 16 contains eight operating circuit boards. The first and second circuit boards 570 contain the triac control circuits for all of the AC drive motors in the main instrument 12. The third and fourth circuit boards 572 contain the Hewlett-Packard HCTL-1,000 DC control circuits for the DC motors in the main instrument. The fifth circuit board 574 contains the analog-to-digital converters for each of the sixteen optical detectors 546 in the vertical photodensitometer 88. The seventh circuit board 578 contains ports used by the computer to communicate with the electronic service module. The eighth circuit board 580 contains ports and connectors for connecting the main unit 12 to the electronic service module 16. The computer and electronic service module also use power supplies which are not illustrated.

Various modifications of the invention are contemplated. Therefore, the above description is not to be read as limiting. For example, the main instrument 12 can be supplied with a single dilution well 582 having a drain which is fluidly connected to the wash station aspiration line 368. Dilutions can be performed in this one cup rather than in separate dilution cups 348 on the dilution cup template 346 for each of the test tubes. Various other modifications can be made to the pumps and motors which drive various components of the main instrument 12 without departing from the teachings of the invention. For example, apparatus other than pressure sensitive membranes may be used in the loading station to determine the vertical placement of an identified test tube. Those skilled in the art will discover other modifications which employ the general principles described hereinabove. Therefore, the scope of the invention is to be determined by the claims which follow.

We claim:

1. An automated patient sample analysis instrument for positively identifying and maintaining the identity of a plurality of patient samples contained in individual sample containers, comprising:
    a container holder having a plurality of receptacles for removably receiving a plurality of sample containers in discrete locations;
    identifying means for identifying a sample container with a patient;
    control means, cooperatively associated with the identifying means, for designating a selected receptacle;
    sensing means for sensing the receipt of an identified sample container in a designated, selected receptacle; and
    preventing means, responsive to the control means and operatively associated with the identifying means and sensing means, for preventing identification of another sample container until the identified sample container is sensed as having been received in the designated, selected receptacle.

2. The instrument of claim 1 wherein the container holder has means for permitting relative downward vertical movement of received sample container and a plurality of pressure-sensitive switches, one switch positioned beneath each receptacle on the container holder so that downward vertical movement of an identified sample container activates the switch therebelow.

3. The instrument of claim 2 wherein the container holder has indexing portions and wherein the sensing means has means for receiving the container holder indexing portions to allow repeatable orientation of the container holder on the sensing means.

4. The instrument of claim 1, wherein the control means automatically preselects the designated, selected receptacle.

5. The instrument of claim 1 for use with reaction plates having a plurality of reaction wells having open tops, located in a regular matrix array of rows and columns, the instrument including transferring means for automatically transferring a portion of each patient sample from each received sample container to a corresponding reaction well, and memory means, operatively associated with the transferring means, for remembering the matrix location of each corresponding reaction well containing a transferred patient sample portion.

6. The instrument of claim 5 wherein the sample transferring means includes:
    a pipette having an open tip end and a diluent receiving end;
    pipette charging means, connected to the diluent receiving end, for precisely charging the pipette with diluent and for establishing and maintaining an air gap between the diluent in the pipette and the patient sample, or a patient sample dilution, drawn through the pipette open tip end;
    pipette control means, operatively associated with the memory means, for dispensing all of the patient sample with a first measured amount of diluent into a dilution cup to form a first dilution, and for drawing a measured portion of the first dilution and dispensing all of the drawn first dilution with a second measured amount of diluent into the corresponding reaction well; and
    automatic means for washing the open tip end prior to the pipette drawing a next patient sample portion.

7. The instrument of claim 6, further including a dilution cup template positionable on the container holder defining a plurality of openings registrable with the container receptacles for passage of the received sample containers therethrough, the template having a plurality of dilution cups, one dilution cup for each container receptacle, the dilution cups having open tops and closed bottoms located interstitially between the openings, wherein the sample transferring means operates to dispense the drawn patient sample and the first measured diluent amount into one of the dilution cups adjacent to the received sample container from which the patient sample was drawn to form the first dilution.

8. The instrument of claim 6 wherein the dilution cup has a drain.

9. The instrument of claim 5, including means for determining the orientation of the container holder relative to the transferring means.

10. The instrument of claim 1 for use with reaction plates having a plurality of reaction wells having open tops, located in a regular matrix array of rows and columns, wherein the reaction wells are contain a first reactant capable of binding with an analyte suspected of being present in the patient samples and wherein the instrument further includes a processing line for sequentially processing the rows of the reaction plates to minimize pressure variations between reaction plate rows, having:

guide means for guiding the reaction plate as the plate advances along a path;

drive means for incrementally advancing the reaction plate along the path in a processing direction with the rows transverse to the path and in timed intervals, each incremental advance having a length approximately equal to the distance between adjacent reaction plate rows;

a temperature-controlled incubation surface, having an entrance end and an exit end, positioned along the path so as to be directly beneath the reaction plate as the plate is advanced and having a width approximately equal to the reaction plate row length to incubate the reaction plate rows as the plate is incrementally advanced;

transferring means for automatically transferring a portion of patient sample from at least some of the received sample containers to a corresponding reaction well in one row of reaction wells adjacent to the incubation surface entrance end with patient samples or dilutions thereof, within the timed interval, wherein the position of the one row adjacent to the incubation surface entrance end defines the beginning of the path;

memory means operatively associated with the transferring means for remembering the matrix location of each corresponding reaction well in the one row containing a transferred patient sample portion;

a first processing station positioned along the path having first removing means for simultaneously removing patient sample and unbound analyte from each reaction well in the one row, first washing means for simultaneously washing each reaction well in the one row, and first adding means for quickly adding a predetermined quantity of a reporter/second reactant conjugate to each reaction well in the one row;

a second processing station, positioned along the path and displaced from the first processing station in the processing direction, having second removing means for simultaneously removing unbound reporter/second reactant conjugate from each reaction well in the one row, second washing means for simultaneously washing each reaction well in the one row, and second adding means for quickly adding a predetermined quantity of a chromogenic substrate to each reaction well in the one row;

stop solution adding means for quickly adding a stop solution to each well in the one row;

determining means, adjacent to the incubation surface exit end, for determining a characteristic of each processed reaction well in the one row wherein the position of the determining means defines the end of the path; and transmitting means, operatively associated with the memory means, for transmitting a signal representative of the determined characteristic of each reaction well in the one row and the corresponding sample container identity to a display device.

11. The instrument of claim 10, further including means for selectively positioning the first and second processing stations along the path relative to the incubation surface entry and exit ends so that a first variable distance between the incubation surface entry end and the first processing station defines a variable first incubation period and so that a second variable distance between the first processing station and the second processing station defines a variable second incubation period.

12. The instrument of claim 11, further including means for selectively positioning the stop solution adding means along the path relative to the second processing station so that a third variable distance therebetween defines a variable third incubation period.

13. The instrument of claim 10 wherein the first and second adding means each include means for locating the position of each well in the one row and means for serially adding the reporter/second reactant conjugate and chromogenic substrate, respectively, to each of the located reaction wells in the one row.

14. The instrument of claim 13 wherein the second serial adding means for mounting the stop solution adding means thereon.

15. The instrument of claim 10 wherein the first and second removing means each include a plurality of elongated aspiration tubes, one aspiration tube for each reaction well in the one row, movable between a retracted position and an extended position, each aspiration tube having a fluid inlet positionable above the reaction well open tops when the aspiration tubes are in the retracted position and positionable adjacent to the reaction well bottoms when the aspiration tubes are in the extended position, each removing means further including vacuum means for establishing a regulated partial vacuum in the aspiration tubes and means for controllably moving the aspiration tubes between the retracted and extended positions, in coordination with the vacuum means, so that the fluid inlets remain in contact with the fluid surface in the reaction wells as the fluid is being removed, whereby a fluid meniscus, formed by fluid surface tension, scrubs the reaction wells dry.

16. The instrument of claim 15 wherein the means for controllably moving the aspiration tubes operates so that the rate at which the fluid meniscus lowers in the reaction wells is equal to the rate at which the aspiration tubes are moved to the extended positions.

17. The instrument of claim 15 wherein the first and second washing means each include a plurality of wash tubes, one wash tube for each reaction well in the one row, each wash tube having a fluid outlet positioned to direct a high-pressure flow of wash solution at an adjacent aspiration tube to impinge on the adjacent aspiration tube and disperse the wash solution into a corresponding reaction well positioned therebelow, and wash tube charging means, operatively associated with the first and second removing means, for charging the wash tubes with successive high-pressure flows of wash solution to vigorously wash the reaction wells and the aspiration tubes.

18. The instrument of claim 17 wherein the aspiration tubes are positioned substantially vertically and wherein the wash tubes are positioned with respect to the aspiration tubes at an angle of approximately 15°.

19. The instrument of claim 17 wherein the wash tubes have an interior diameter of approximately 0.027 inch and the wash tubes charging means includes a solenoid-operated liquid pump having a displacement sufficient to deliver approximately 0.125 ml wash solution to each wash tube and a displacement stroke period of approximately 100-200 milliseconds when the solenoid is energized to achieve the high-pressure flows of wash solution.

20. The instrument of claim 10 wherein the determining means has an optical photodensitometer having a plurality of optical filters having different light-transmission characteristics.

21. An automatic patient sample analysis instrument for positively identifying and maintaining the identity of a plurality of patient samples contained in individual sample containers, comprising:
   a container holder having indexing portions and a plurality of receptacles for removably receiving the sample containers in discrete locations;
   an identifying device generating a unique signal, indicative of an identified sample container, wherein the identified sample container is to be received in a selected receptacle;
   a sensor array having indexing portions matable with the container indexing portions for orienting the container holder on the sensor array, and having a plurality of sensors positioned at the discrete locations to detect the receipt of the identified sample container in the selected receptacle; and
   a control system, operatively associated with the identifying device and sensor array, having a signal processor processing the unique signals and preventing identification of another sample until the identified sample is sensed as having been received in the selected receptacle, a memory remembering the discrete location of the received sample container, and an indicator indicating to an operator that the identified sample container has been received in the selected receptacle.

22. The instrument of claim 21 for use with reaction plates having a plurality of reaction wells with open tops at known locations, wherein the instrument includes a patient sample transfer system, operatively associated with the control system, tranferring a portion of each patient sample to a corresponding one of the reaction wells, having:
   a linear reaction plate conveyor having reaction plate guides guiding the reaction plate in a processing direction, a reaction plate conveyor drive to advance the reaction plate on the reaction plate guides, and a reaction plate position sensor generating a reaction plate position signal;
   a linear container holder conveyor, positioned substantially parallel to the reaction plate conveyor, having container holder guides guiding the container holder, a container holder conveyor drive to advance the container holder on the container holder guides, and a container holder position sensor generating a container holder position signal;
   a horizontal cross member, positioned substantially transverse to the conveyors and sufficiently above the conveyors to allow the reaction plate and container holder to pass therebelow when advanced;
   a horizontally movable pipette carriage, movably positioned on the horizontal cross member, having a horizontal position sensor generating a pipette carriage position signal and a pipette carriage drive;
   a vertically movable automatic pipette, positioned on the horizontally movable pipette carriage, having a diluent receiving end and an open tip end, and a fluid level sensor, adjacent to the tip open end, generating a fluid level signal, and an automatic pipette drive;
   a diluent control mechanism having an automatic precision syringe fluidly connected to an automatic two-position valve having a supply port connected to a diluent supply and a pipette port fluidly connected to the pipette diluent receiving end, a valve position sensor generating a valve position signal, and a syringe position sensor generating a syringe position signal; and
   a transmitter transmitting the reaction plate position signal, container holder position signal, pipette carriage position signal, and fluid level signal to the signal processor, wherein the control system operates the reaction plate conveyor drive, the container holder conveyor drive, the pipette carriage drive, the automatic pipette drive, the automatic two-position valve, and the automatic precision syringe to transfer a portion of at least some of the patient sample from the received sample containers to the corresponding reaction wells at the known locations wherein the control system memory remembers the known location for each transferred patient sample position.

23. An automated patient sample analysis instrument for positively identifying and maintaining the identity of a plurality of patient samples contained in individual sample containers for use with reaction plates having a plurality of reaction wells having open tops, located in a regular matrix array of rows and columns, comprising:
   a container holder having a plurality of receptacles for removably receiving the sample containers in discrete locations;
   identifying means for identifying a sample container with a patient;
   sensing means for sensing the receipt of an identified sample container in a selected receptacle;
   preventing means, operatively associated with the identifying means and sensing means, for preventing identification of another sample container until the identified sample container is sensed as having been received in the selected receptacle;
   two independent processing lines having means for independently processing two reaction plates;
   transferring means for automatically transferring a portion of each patient sample from each received sample container to a corresponding reaction well in each of the two reaction plates;
   memory means, operatively associated with the transferring means, for remembering the matrix location of each corresponding reaction well of each of the two plates containing a transferred patient sample portion.

* * * * *